United States Patent [19]

Hoffmann et al.

[11] Patent Number: 5,895,660

[45] Date of Patent: *Apr. 20, 1999

[54] DEUTERATED ACTIVE SUBSTANCES IN TRANSDERMAL APPLICATION

[75] Inventors: Hans-Rainer Hoffmann; Thomas Hille; Andreas Koch, all of Neuwied; Rudolf Matusch, Marburg, all of Germany

[73] Assignee: LTS Lohmann Therapie-Systeme GmbH, Neuwied, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/666,269

[22] PCT Filed: Dec. 6, 1994

[86] PCT No.: PCT/EP94/04047

§ 371 Date: Aug. 15, 1996

§ 102(e) Date: Aug. 15, 1996

[87] PCT Pub. No.: WO95/17188

PCT Pub. Date: Jun. 29, 1995

[30] Foreign Application Priority Data

Dec. 22, 1993 [DE] Germany ................... 43 43 838

[51] Int. Cl.$^6$ ................................................. A61F 13/00
[52] U.S. Cl. .................. 424/449; 424/434; 424/448; 514/946; 514/947; 514/969
[58] Field of Search ...................... 424/448, 449, 424/434; 514/946, 947, 969

[56] References Cited

U.S. PATENT DOCUMENTS

| 3,598,122 | 8/1971 | Zaffaroni | 128/268 |
| 4,473,585 | 9/1984 | Abrahamsson | 424/318 |
| 4,529,600 | 7/1985 | Dawson | 514/529 |
| 4,898,855 | 2/1990 | Baggiolini | 514/167 |
| 5,075,337 | 12/1991 | Cordi | 514/626 |

FOREIGN PATENT DOCUMENTS

| 3 315 272 | 3/1986 | Germany. |
| 3 843 239 | 2/1990 | Germany. |

OTHER PUBLICATIONS

Aldrich's Catalogue Handbook of Fine Chemicals, pp. 126 and 1024, 1992.

Sigma's Biochemicals and Organic Compounds for Research and Diagnostics, pp. 1637–1638, 1992.

Heilmann, "Therapeutische Systeme –Konzept und Realisation programmierter Arzneiverabreichung", 4th Edition Ferdinand Enke Verlag Stuttgart 1984, page 26.

Primary Examiner—D. Gabrielle Brouillette
Attorney, Agent, or Firm—Wenderoth, Lind & Ponack, L.L.P.

[57] ABSTRACT

A drug for the release of active substances to the skin, which has an increased deuterium portion as compared to the natural isotope distribution.

13 Claims, 8 Drawing Sheets

DEUTERATED ACTIVE SUBSTANCES IN TRANSDERMAL APPLICATION

This application is a 371 of PCT/EP94/04047, filed Dec. 6, 1994.

BACKGROUND OF THE INVENTION

The present invention relates to the transdermal application of deuterated drugs. Although the transdermal application of drugs undoubtedly has great advantages, there is the disadvantage that the amount of drug that can be absorbed via the skin is limited. Thus, when the therapy by dermal application began, attempts were made at the same time to find a way of increasing the capacity of drugs to penetrate through the skin. The development of penetration enhancers which are added to drugs for dermal application was regarded as a solution for this problem first. These substances change subjacent skin structures, at least for a short time, and can result in undesired side effects in unfavorable cases. Other possibilities of increasing the absorption of active substances is to remove the stratum corneum by a laser treatment or by repeated sticking and tearing-off adhesive strips, the so-called "stripping". The drawback of this method is the fact that not only the desired penetration of the active substance into the human body is facilitated but also that of all other substances as well as of micro-organisms, such as bacteria and fungus spores. Another way of improving the dermal absorption is to use current. As is known to medical experts, this process, known under the term "iontophoresis", cannot be applied without pain. The same applies to the so-called "spiked patch". This administration form is fixed to the body by means of cannulae penetrating the horny layer of the skin. The active substance release takes place through said cannulae which simultaneously serve as fixation aids.

The dermal application of so-called "pro-drugs" seems at first to be an interesting alternative. In this case structural elements of drugs which are considered to be particularly unfavorable for the dermal absorption, e.g., phenolic hydroxyl groups, are derivatized, e.g., esterified. The characteristic feature of the chemical modification of pro-drugs is the fact that the derivatization is extremely unstable so that the drug underlying the pro-drug is quickly and completely formed in vitro. However, it is known to the skilled artisan that this actually neat idea can only rarely be realized in practice, since the intended quick and complete metabolic degradation does not take place in vivo. Thus, some toxicological questions arise with respect to the pro-drugs which still require extensive pharmacologic studies.

By way of trial, radioactively labeled drugs were applied transdermally in the past, in order to facilitate the determination of the extremely low blood levels frequently occurring after transdermal application; an exchange of radioactive components under in-vivo-conditions was not intended to take place.

DESCRIPTION OF THE INVENTION

Accordingly, it is the object of the present invention to provide a drug composition for the transdermal application of active substances, which allows an increased absorption rate for active substances and avoids the drawbacks known from methods according to the art. According to the present invention this object is achieved in a surprising manner by means of a drug for the release of active substances to the skin, which has an increased deuterium portion as compared to the natural isotope distribution.

This solution is most surprising since deuterated compounds, as compared to corresponding non-deuterated substances, should actually have a worse or—at best—the same diffusion behavior owing to their increased molecular weight.

Within the meaning of the present invention deuterated compounds mean those compounds in which at least one or several hydrogen atoms are replaced by deuterium.

The subject matter of the present invention are compounds which are not labeled isotopically and are required for studies on biosynthesis and biodegradation of natural substances, works on the metabolism of drugs and other chemicals in plant and animal organisms, since these have to be stable. However, in the present invention a re-exchange reaction is very well possible in such a way that the introduced deuterium atoms are replaced again by hydrogen atoms in the body by an exchange reaction. It is known to the skilled artisan that hydrogen always represents an isotopic mixture of $^1H$, $^2D$, and $^3T$. For this reason, all chemical compounds comprising hydrogen are always present as a mixture of deuterated and non-deuterated compounds, with the portion of $^2D$ amounting to about 0.015 mole-%. A preferred embodiment of the present invention are mixtures in which the portion of deuterated compounds is considerably increased, i.e., to at least 10 mole-%. Additionally preferred are those drugs in which the portion of deuterium, relative to exchangeable hydrogen isotopes, amounts to at least 10 mole-%.

The term drugs is known to the skilled artisan. For application purposes to the skin or mucous membranes (e.g., nose, eye) ointments which represent gels having a plasticity are suitable as well as pastes which can be referred to as ointments having a high solids content. For obvious reasons, these administration forms must not comprise protic solvents, such as water or ethanol.

According to Zaffaroni, a transdermal therapeutic system (TTS) is "a drug-containing device or administration form" continuously releasing one or several drug/s at a predetermined rate over a given period to a determined application site (cited according to Heilmann, "Therapeutische Systeme—Konzept und Realisation programmierter Arzneiverabreichung", 4th edition, Ferdinand Enke Verlag Stuttgart 1984, page 26), with the skin being the site of application in the present case.

The structure of transdermal therapeutic systems is known to those skilled in the art. Patents describing the basic structure include, for example, DE 33 15 272, DE 38 43 239, U.S. Pat. No. 3,598,122.

When a transdermal therapeutic system is applied to the skin of a patient, the drug is released to take a topic or systemic effect on the patient. Administration forms of this kind are already used in therapy. They usually have a layered structure, and in the most simple case they consist of a backing layer, a self-adhesive active substance reservoir and a removable protective layer which must be removed prior to application.

Substances used as active agents are those causing a local or systemic effect when applied to the skin either without or with absorption filters.

Substances having a local effect include, for example, antiperspirants, fungicides, bactericides, and bacteriostats.

Substances having a systemic effect include, for example, antibiotics, hormones, antipyretics, antidiabetics, coronary vasodilators, cardio-active glycosides, spasmolytics, antihypertensives, psychotropic drugs, migraine analgesics, corticoids, analgesics, contraceptives, antirheumatics, anticholinergics, sympatolytics, sympatomimetics, vasodilators, anticoagulants, and antiarrhythmics.

In order to allow a re-exchange reaction in the human body those hydrogen atoms have to be replaced by deuterium which are exchangeable by a treatment with deuterium oxide (recrystallization, extraction by shaking etc.), e.g., hydrogen atoms in O—H or N—H bonds.

The present invention will be illustrated by the following examples.

1. PRODUCTION OF THE DEUTERATED COMPOUNDS

1.1 Production of Deuterated Morphine Base 100 mg morphine base monohydrate is dissolved in 90 ml super-pure deuterium oxide in the boiling heat. The mixture is allowed to cool to room temperature, with gradual formation of white, needle-like crystals, after separation to constant weight they are dried in the desiccator.

yield: 64 mg=64% of theory melting range: from 235° C. (morphine base: from 235° C.)

Figure 1:
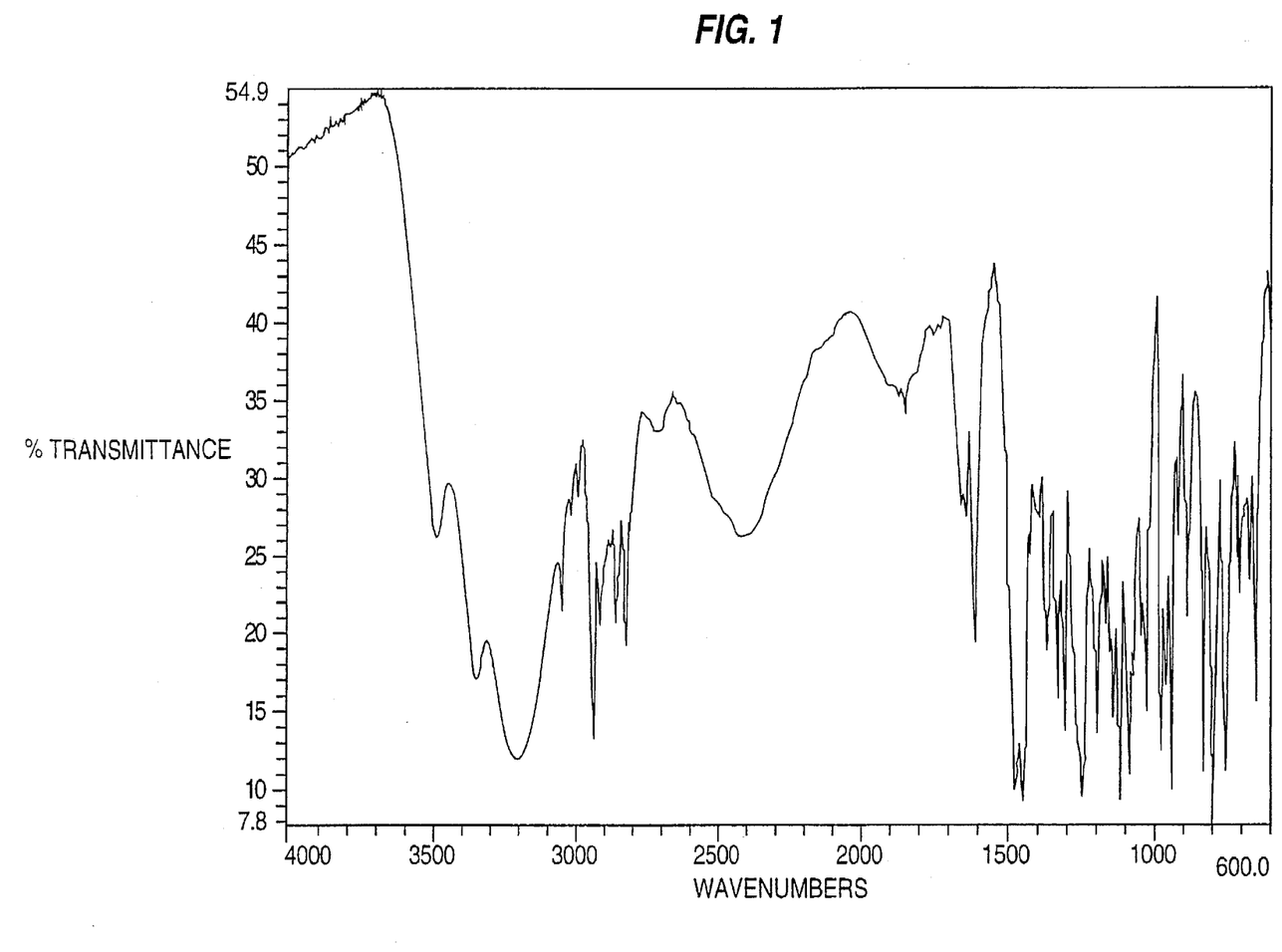
FIG. 1 IR-spectrum of morphine base monohydrate
Figure 2:
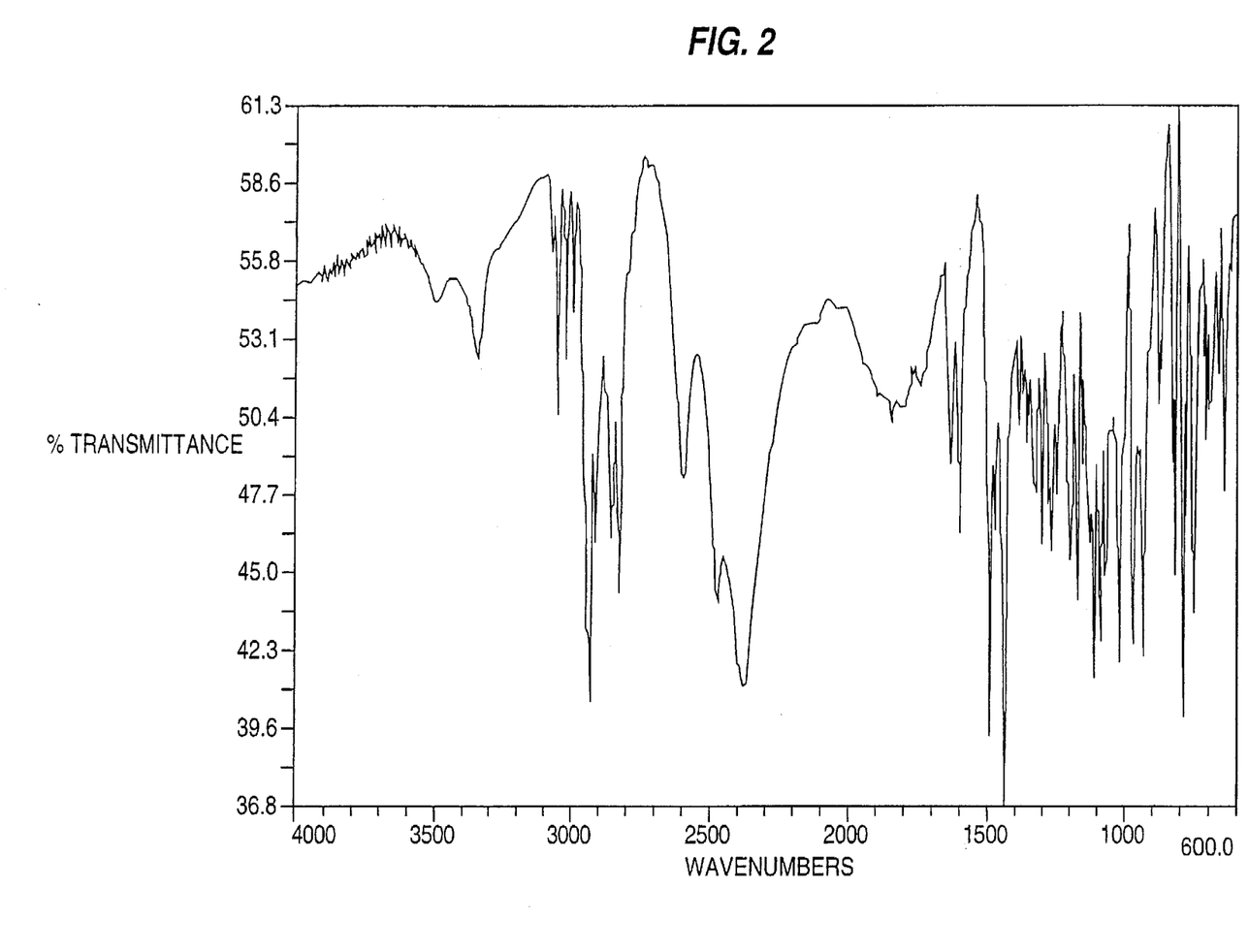
FIG. 2 IR-spectrum of deuterated morphine base

The infrared spectra of educt and product are shown in FIGS. 1 and 2.

The bands of the O—H and O—D stretching vibrations, respectively, show that the deuteration degree amounts to about 95%, relative to exchangeable hydrogen atoms.

1.2. Production of Deuterated Oleic Acid 10 g oleic acid corresponding to NF XVII according to USP XXXII is mixed with 40 g deuterium oxide and intimately stirred at room temperature for several hours. The solution is decanted, and the oleic acid phase is vacuum-dried.

1.3 Production of Deuterated Salbutamol 0.5 g salbutamol is dissolved under heating in 20 g deuterium oxide. Since the substance does not crystallize, evaporation under vacuum at room temperature is carried out.

yield: 0.5 g flash point: 149.8° C. (flash point salbutamol: 153.4° C.)

Figure 3:
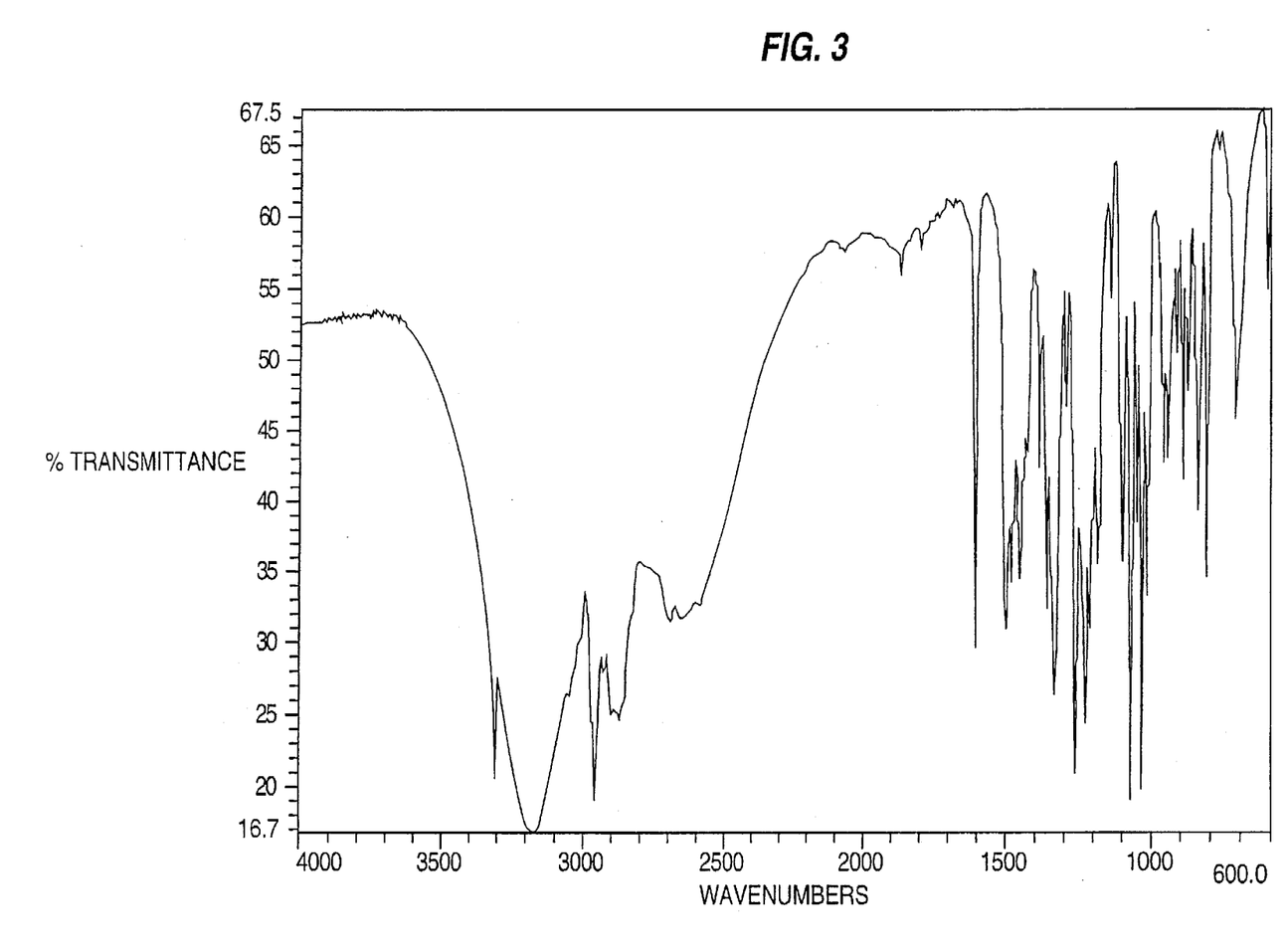
FIG. 3 IR-spectrum of salbutamol
Figure 4:
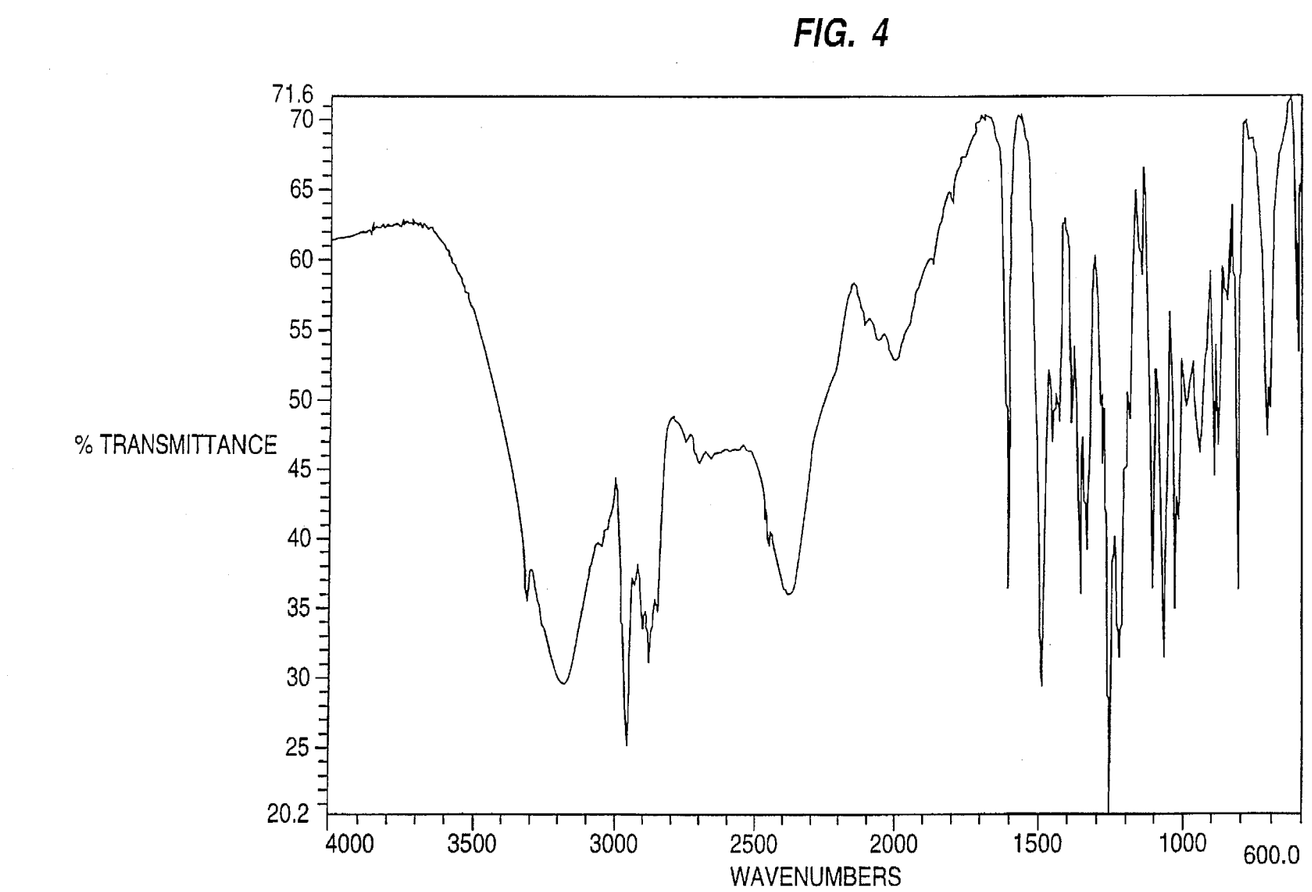
FIG. 4 IR-spectrum of deuterated salbutamol

The IR-spectra of educt and product are shown in FIGS. 3 and 4.

The IR-spectra show that the deuteration degree nearly amounts to 100%, relative to exchangeable hydrogen atoms.

1.4 Production of Deuterated Benzoic Acid 2.0 g benzoic acid is recrystallized from 45 ml boiling deuterium oxide.

yield: 1.86 g flash point: 120.3° C. (flash point benzoic acid: 122.8° C.)

Figure 5:
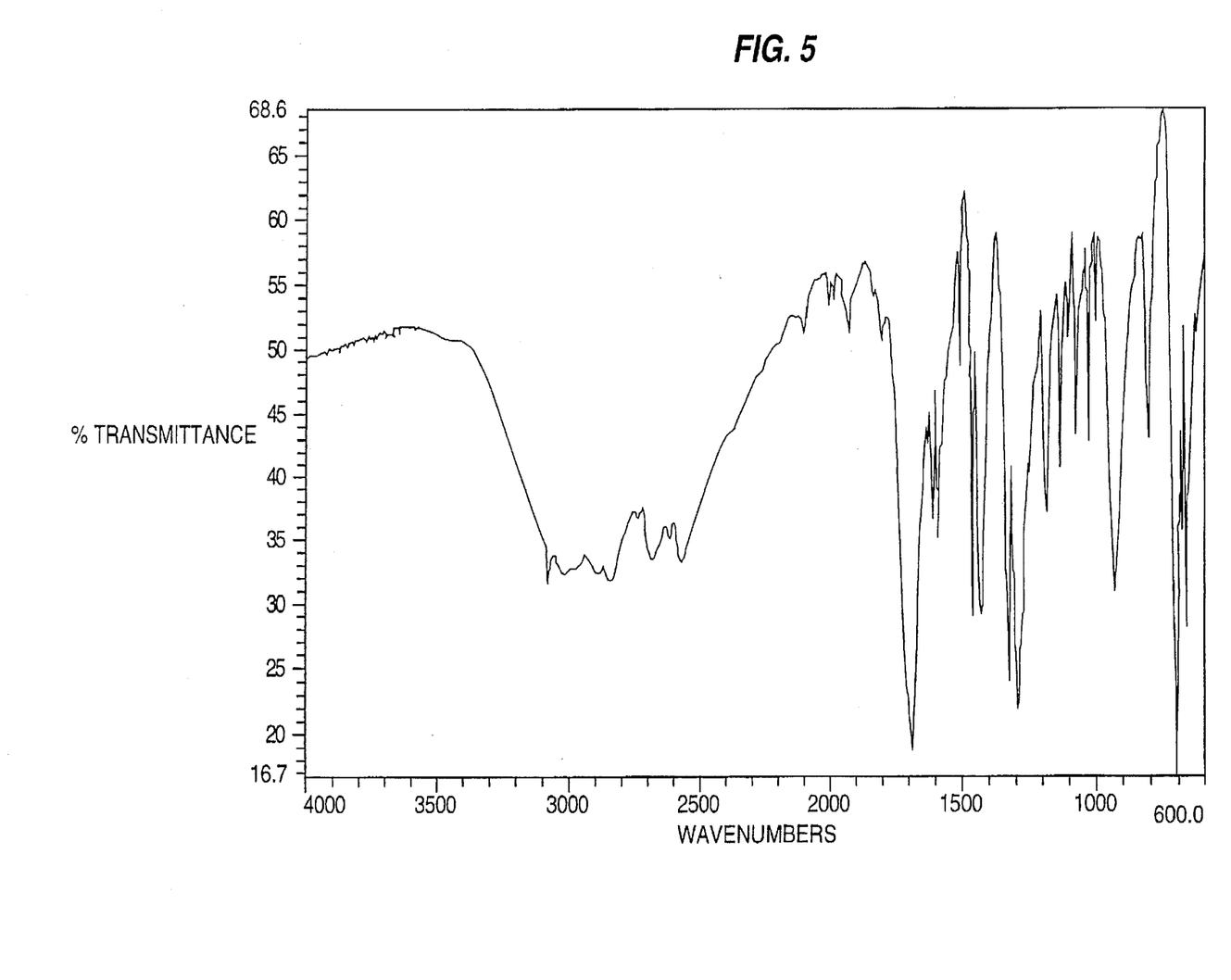
FIG. 5 IR-spectrum of benzoic acid
Figure 6:
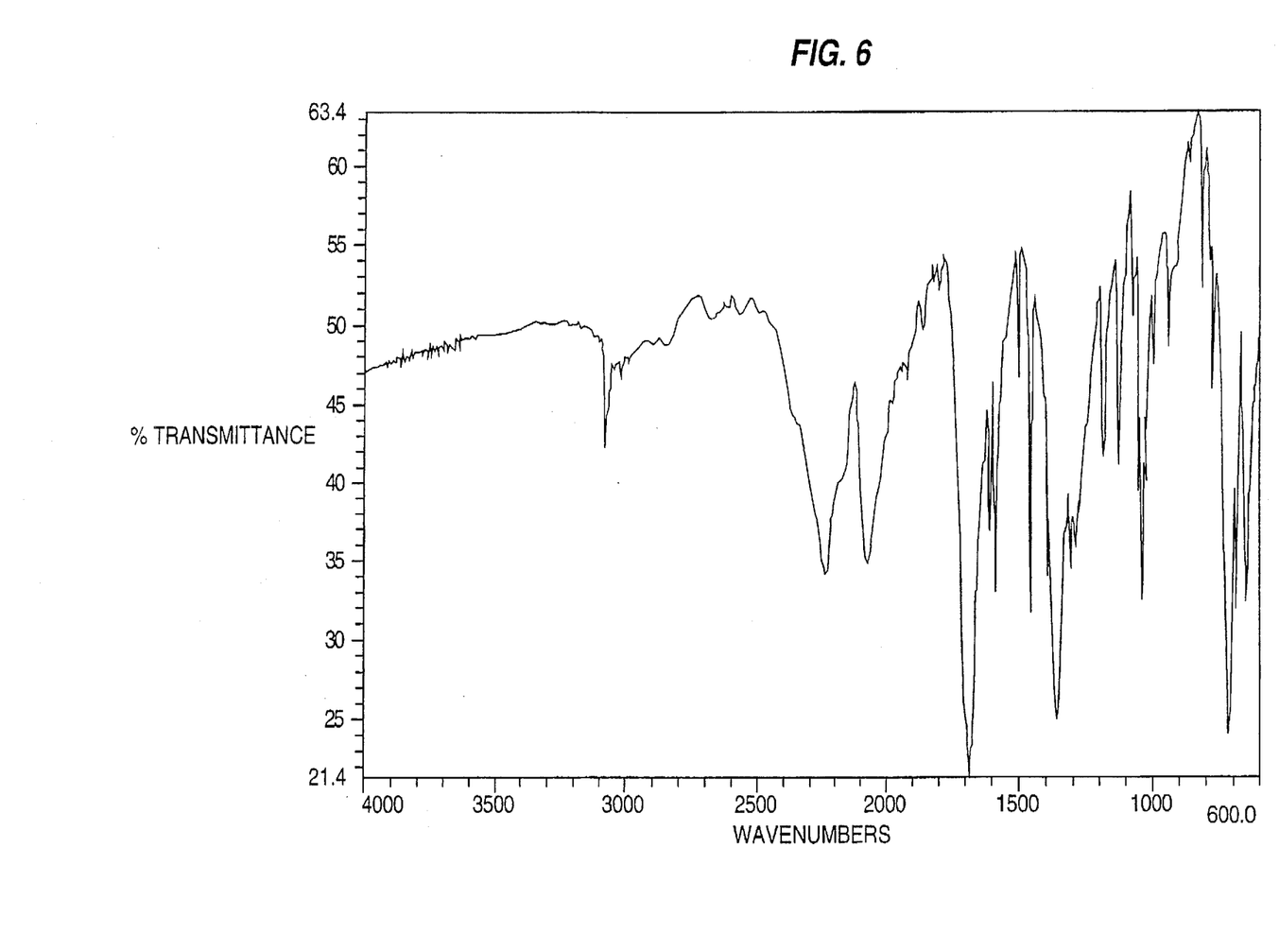
FIG. 6 IR-spectrum of deuterated benzoic acid

The IR-spectra of educt and product are shown in FIGS. 5 and 6.

It can be seen that the deuteration degree nearly amounts to 100%.

1.5 Production of Deuterated Phenol 5.0 g phenol is mixed with 5.0 g deuterium oxide and heated. Subsequently, deuterium oxide in water admixture is sucked off under vacuum.

Figure 7:
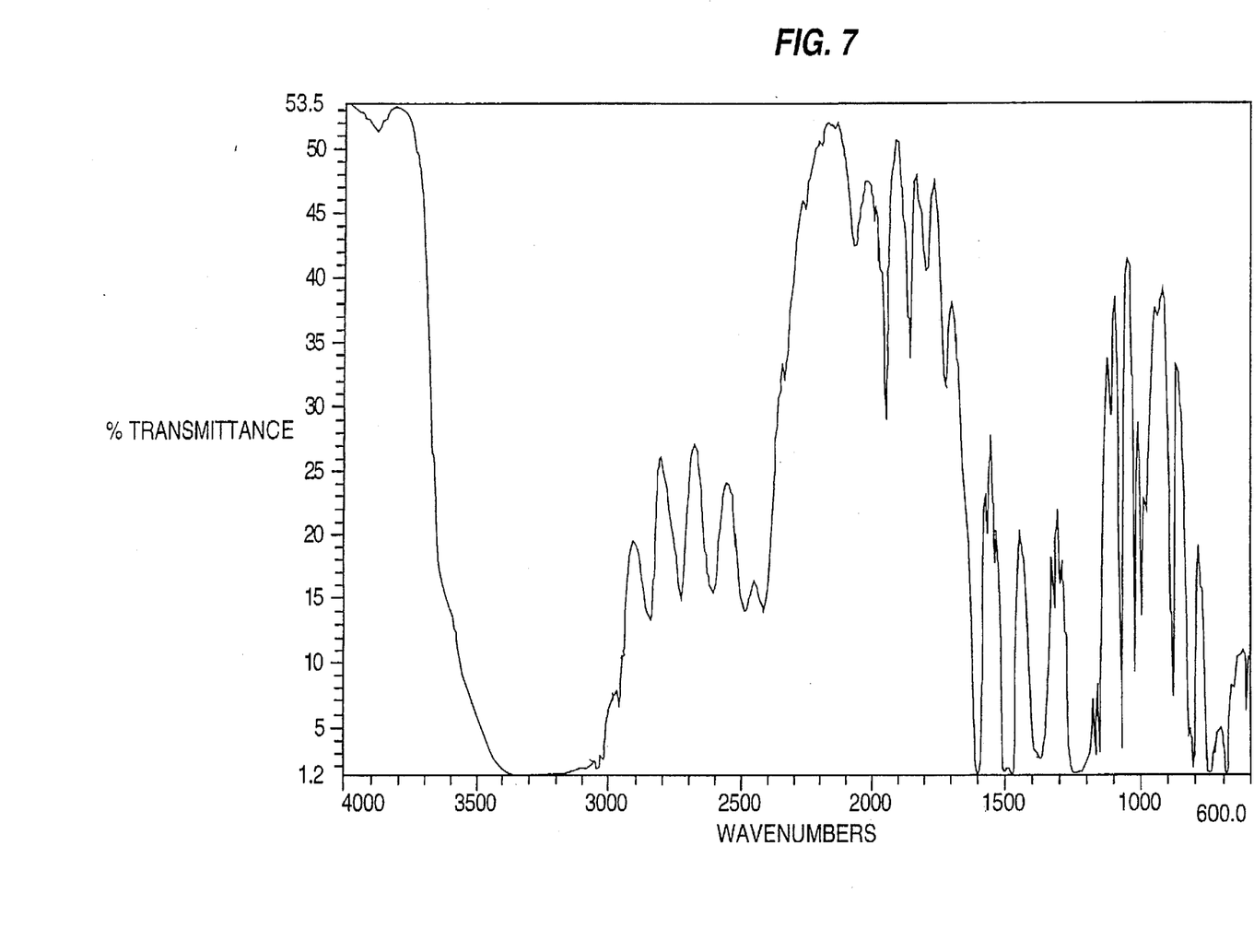
FIG. 7 IR-spectrum of phenol
Figure 8:
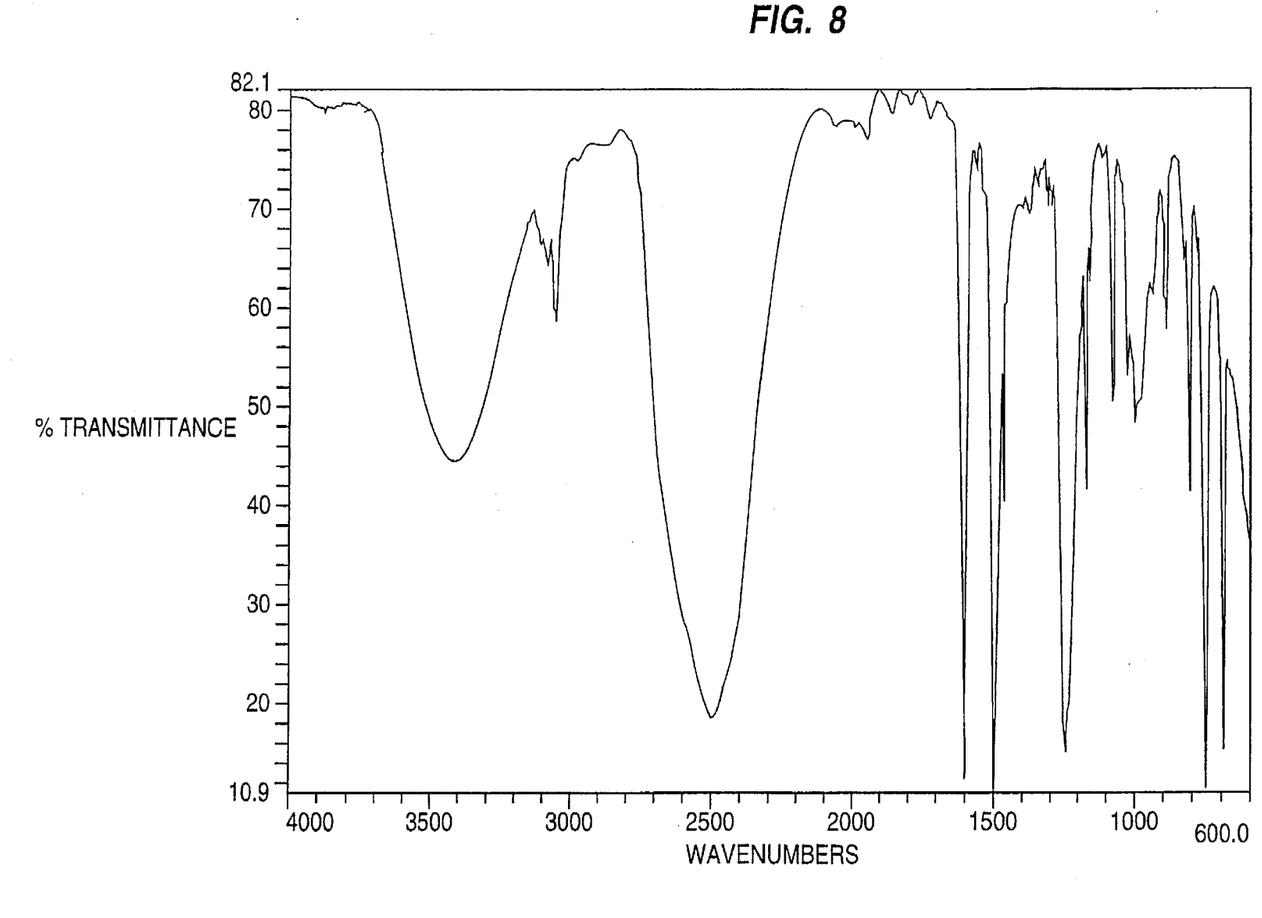
FIG. 8 IR-spectrum of deuterated phenol

The IR- spectra of educt and product are shown in FIGS. 7 and 8.

It can be seen that the deuteration degree nearly amounts to 100%.

The spectra listed in the following clearly show that the bands caused by the stretching vibrations of the two hydroxyl groups were shifted to lower wavenumbers; this was to be expected owing to the higher atomic weight of $^2D$ towards $^1H$. Thus, the detection of the exchange can be provided by IR spectroscopy.

2. IN-VITRO-PERMEATION

2.1.1 Dissolution of Morphine Base 400 mg deuterated morphine base (cf. Ex. 1.1.) is dissolved in 1600 mg deuterated oleic acid (cf. Ex. 1.2) and 1 g deuterated methanol ($D_3C$—OD) (cf. 1.2).

After dissolution the deuterated methanol is removed under vacuum.

A morphine/oleic acid solution is prepared analogously from non-deuterated compounds.

2.1.2. Dissolution of Salbutamol 200 mg deuterated salbutamol (cf. Ex. 1.3) is dissolved in 800 mg deuterated oleic acid (cf. Ex. 1.2.) and 2 g 2-butanone. After dissolution the 2-butanone is removed under vacuum (cf. 1.2).

A salbutamol/oleic acid solution is prepared from non-deuterated compounds in the same way.

2.1.3. Dissolution of Benzoic Acid 0.5 g deuterated benzoic acid (cf. Ex. 1.4) is dissolved in 4.5 g dimethylisosorbite. A solution of non-deuterated benzoic acid is prepared analogously.

2.1.4. Dissolution of Phenol 0.5 g deuterated phenol (cf. Ex. 1.5) is dissolved in 4.5 g dimethylisosorbite.

A solution of non-deuterated phenol is prepared analogously.

2.2 Penetration Experiments

The experiments are conducted with excised guinea pig skin clamped in a Franz' diffusion cell. Physiologic saline is used as acceptor medium, the determinations of content are carried out by HPLC. The results are listed in the Tables below.

Results of the penetration experiments 2.2.1 Salbutamol

TABLE 1

Results of penetration of salbutamol and deuterated salbutamol with excised skin of guinea pigs.

|  | 3 h | 5 h [µg/cm$^2$] | 7 h [µg/cm$^2$] | 24 h [µg/cm$^2$] |
|---|---|---|---|---|
| Salbutamol |  | 14 | 19 | 467 |
| deuterated salbutamol |  | 23.0 | 49.0 | 1067 |

2.2.2 Morphine

TABLE 2

Results of penetration of morphine and deuterated morphine using excised skin of guinea pigs.

|  | 6 h [µg/cm$^2$] | 18 h [µg/cm$^2$] | 22 h [µg/cm$^2$] | 26 h [µg/cm$^2$] |
|---|---|---|---|---|
| Morphine | 2.6 | 84 | 153 | 256 |
| deut. morphine | 5.3 | 103 | 187 | 299 |

It can be seen that all values of the deuterated form prove an increased flux.

2.2.3 Benzoic Acid

TABLE 3

Results of penetration of benzoic acid and deuterated benzoic acid with excised skin of guinea pigs.

|  | 2 h [µg/cm$^2$] | 4 h [µg/cm$^2$] | 8 h [µg/cm$^2$] | 24 h [µg/cm$^2$] |
|---|---|---|---|---|
| Benzoic acid | 54 | 252 | 1022 | 1700 |
| deut. benzoic acid | 73 | 320 | 1249 | 2483 |

2.2.4 Phenol

TABLE 4

Results of penetration of phenol and deuterated phenol with excised skin of the yucatan-micro-pig.

|  | 2 h [µg/cm$^2$] | 4 h [µg/cm$^2$] | 8 h [µg/cm$^2$] | 24 h [µg/cm$^2$] |
|---|---|---|---|---|
| Phenol | 2 | 7.9 | 46.4 | 487 |
| deut. phenol | 2 | 13 | 74 | 701 |

The application on the skin of the yucatan-micro-pig was necessary since phenol has a necrotic and a keratolytic effect. Due to this leveling effect the difference between deuterated and non-deuterated phenol would possibly have not become detectable.

The obtained flux does not only show that an increased permeation rate can be achieved by the replacement of hydrogen by deuterium but also that the effect is the higher the more hydrogen atoms are exchanged (cf. benzoic acid/salbutamol).

We claim:

1. In a pharmaceutical composition for dermal or mucosal application which comprises an active substance for penetration through the skin of a patient, wherein said active substance has at least one OH- or NH-group or having at least one OH- and one NH-group, the improvement comprises the active substance has at least 10 mole % deuterium bound to the oxygen atom of the said OH-group, or the nitrogen atom of the said NH-group, or bound to both the oxygen atom of the said OH-group and to the nitrogen atom of the said NH-group.

2. A pharmaceutical composition according to claim 1, wherein said composition comprises an additional active substance having a natural hydrogen isotope distribution.

3. A composition according to claim 2, wherein the amount of said active substance having at least 10 mole % deuterium is at least 10 mole-% of the active substances.

4. A pharmaceutical composition according to claim 1, wherein said active substance contains at least 10% deuterium relative to the hydrogen bound to the oxygen or the nitrogen, or both the oxygen and nitrogen atoms of the OH-group, NH-group, or the OH- and NH-groups, respectively.

5. A composition according to claim 1, in the form of an ointment or paste.

6. In a transdermal system which comprises a backing layer, an active substance reservoir and a removable protective layer, the improvement wherein the active substance reservoir contains a composition as defined in claim 1.

7. A method of dermally or mucosally treating a patient with a pharmaceutical composition comprising an active substance having at least one OH- or NH-group or having at least one OH- and one NH-group, which comprises applying to the skin or mucosa of the patient a composition containing an active substance having at least 10 mole % deuterium bound to the oxygen atom of the said OH-group, or the nitrogen atom of the said NH-group, or bound to both the oxygen atom of the OH-group and to the nitrogen atom of the NH-group, wherein the active substance has an increased portion of deuterium as compared to the natural isotope distribution of the active substance, which increases the skin penetration of said active substance.

8. A method according to claim 7, wherein said composition comprises an additional active substance having a natural hydrogen isotope distribution.

9. A method according to claim 8, wherein the amount of said active substance having at least 10 mole % deuterium is at least 10 mole-% of the active substances.

10. A method according to claim 7, wherein the composition is contained in an ointment or paste.

11. A method according to claim 7, wherein the composition is contained in a transdermal therapeutic system, comprising a backing layer, a reservoir layer and a removable protective layer.

12. A method according to claim 7, wherein said active substance contains at least 10% deuterium, relative to the hydrogen bound to the oxygen or the nitrogen, or both the oxygen and nitrogen atoms of the OH-group, the NH-group, or the OH- and NH-groups, respectively.

13. A method of improving the skin or mucosa penetration of a pharmaceutically active substance, having at least one OH- or NH-group or at least one OH- and one NH-group, which comprises a) replacing at least 10 mole % of the hydrogen atoms of said OH- or NH-group, or OH- and NH-groups, with deuterium atoms so that the said active substance has an increased deuterium amount as compared to the natural hydrogen isotope distribution of the active substance, and b) applying to the skin or mucosa of a patient a pharmaceutical composition comprising the said active substance having an increased deuterium amount as compared to the natural hydrogen isotope distribution.

* * * * *